(12) United States Patent
Hynynen et al.

(10) Patent No.: US 6,514,221 B2
(45) Date of Patent: Feb. 4, 2003

(54) BLOOD-BRAIN BARRIER OPENING (75) Inventors: Kullervo H. Hynynen, Medfield, MA (US); Nathan J. McDannold, Roxbury, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/915,599

(22) Filed: Jul. 26, 2001

(65) Prior Publication Data

US 2002/0038086 A1 Mar. 28, 2002

Related U.S. Application Data (60) Provisional application No. 60/221,064, filed on Jul. 27, 2000.

(51) Int. Cl.$^7$ .............................................. A61H 1/100
(52) U.S. Cl. .......................................................... 601/2
(58) Field of Search ............................... 600/437, 439, 600/458; 601/2; 424/9.1–9.81

(56) References Cited

U.S. PATENT DOCUMENTS

| | | | | |
|---|---|---|---|---|
| 5,149,319 A | * | 9/1992 | Unger | 424/450 |
| 5,540,909 A | * | 7/1996 | Schutt | 424/9.51 |
| 5,752,515 A | * | 5/1998 | Jolesz et al. | 600/411 |
| 6,066,123 A | * | 5/2000 | Li et al. | 424/450 |
| RE36,939 E | * | 10/2000 | Tachibana et al. | 424/94.6 |
| 6,135,976 A | * | 10/2000 | Tachibana et al. | 604/101.03 |
| 6,264,917 B1 | * | 7/2001 | Klaveness et al. | 424/9.52 |
| 6,346,098 B1 | * | 2/2002 | Yock et al. | 514/2 |
| 6,416,740 B1 | * | 7/2002 | Unger | 424/450 |

OTHER PUBLICATIONS

Kullervo Hynynen, Review of Ultrasound Therapy, IEEE Ultrasonics Symposium, 1997, p. 1305–1313.*

* cited by examiner

Primary Examiner—Francis J. Jaworski
Assistant Examiner—William Jung
(74) Attorney, Agent, or Firm—Mintz, Levin, Cohn, Ferris, Glovsky and Popeo, P.C.

(57) ABSTRACT

A method of opening a blood-organ barrier of a subject includes providing an exogenous agent configured to facilitate opening of the blood-organ barrier, administering the exogenous agent to a desired region of the subject, and applying energy to the desired region of the subject while the exogenous agent is present in the desired region, the energy being in a blood-organ-barrier-opening amount sufficient to induce opening of the blood-organ barrier of the subject with the exogenous agent present and below a damage amount sufficient to induce thermal damage to tissue in the absence of the exogenous agent.

26 Claims, 7 Drawing Sheets

BLOOD-BRAIN BARRIER OPENING

CROSS-REFERENCE TO RELATED ACTIONS

This application claims the benefit of U.S. Provisional Application Ser. No. 60/221,064 filed Jul. 27, 2000 and entitled "Noninvasive Image-Guided Opening of Blood Brain Barrier."

STATEMENT AS TO FEDERALLY-SPONSORED RESEARCH

This invention was made at least in part with Government support under Grant No. CA 76550, awarded by the National Institutes of Health. The Government has certain rights in this invention.

FIELD OF THE INVENTION

The invention relates to opening of the blood-brain barrier, and more particularly to noninvasive techniques for doing so.

BACKGROUND OF THE INVENTION

Ultrasound systems transmit energy at ultrasound frequencies into a desired subject. The signals can be detected and processed to produce images of the subject. The signals can also be concentrated or focused in such a way as to ablate, or induce cavitation in, a selected region of the subject. For any of these uses, an array of transducers is often used to provide the signals, and to focus the ultrasound energy in a desired manner to either image the subject or to ablate or otherwise provide ultrasound therapy to the subject. By using ultrasound, regions of a patient's body can be imaged or treated in a noninvasive manner, reducing cost and risk to the patient, especially when imaging or treating sensitive areas of the patient such as the brain.

The blood vessels in the brain include endothelial cells connected by "tight junctions" in what is known as the Blood-Brain Barrier (BBB). The BBB inhibits substances in the blood flow of a subject from entering the subject's brain. While this is often desirable, e.g., by reducing illness, it is often a nuisance, e.g., by inhibiting delivery of drugs to the brain to help, not hinder, the subject. For example, in spite of a large number of very potent drugs, many central nervous system diseases are difficult to treat due to the inability of these substances to penetrate the BBB. Similarly, the BBB is a major limitation for genetherapy in the brain. Some other organs also contain tight junctions that limit drug delivery. Thus, the body contains multiple blood-organ barriers.

Various options for opening the BBB are available. Drugs can be made to penetrate the BBB, e.g., by making the drugs lipophilic, or by using carriers such as amino acid and peptide carriers. Another option is to physically open the BBB tight junctions temporarily. Chemicals can be administered to the brain to open the tight junctions of the BBB. For example, osmotic opening is possible using an intra-carotid arterial injection of hypertonic solution to shrink the endothelial cells and open the tight junctions. Drug "cocktails" may also open the BBB, and may do so in a more time-controlled manner than osmotic opening. In both the osmotic and chemical opening techniques, an intra-arterial catheter insertion is used and the BBB in the whole brain opens. More localized opening can be achieved by inserting a catheter into the brain and infusing an opening agent directly to a targeted area.

SUMMARY OF THE INVENTION

In general, in an aspect, the invention provides a method of opening a blood-organ barrier of a subject. The method includes providing an exogenous agent configured to facilitate opening of the blood-organ barrier, administering the exogenous agent to a desired region of the subject, and applying energy to the desired region of the subject while the exogenous agent is present in the desired region, the energy being in a blood-organ-barrier-opening amount sufficient to induce opening of the blood-organ barrier of the subject with the exogenous agent present and below a damage amount sufficient to induce thermal damage to tissue in the absence of the exogenous agent.

Implementations of the invention may include one or more of the following features. The energy applied is ultrasound energy and the exogenous agent contains at least one of gaseous bubbles, a high concentration of gas, solid particles configured to vaporize in response to body temperature, solid particles configured to vaporize in response to the ultrasound energy, liquid configured to vaporize in response to body temperature, liquid configured to vaporize in response to the ultrasound energy, micro particles configured to act as cavitation sites, solid particles having higher acoustic impedance than tissue in the desired region, and liquid with a high acoustic absorption coefficient. The blood-organ-barrier-opening amount is less than approximately one order of magnitude lower than the damage amount. The blood-organ-barrier-opening amount is less than approximately two orders of magnitude lower than the damage amount.

Implementations of the invention may further include one or more of the following features. The exogenous agent is administered to the subject without penetrating a skull of the subject. The exogenous agent is administered through a vasculature of the subject. The administering includes waiting for the exogenous agent to reach the desired region via the vasculature.

Implementations of the invention may further include one or more of the following features. The method further includes imaging at least the desired region of the subject and determining if the blood-organ barrier has opened in the desired region using results of the imaging. The applying includes adjusting at least one characteristic of the ultrasound energy to apply at least the blood-organ-barrier-opening amount to the desired region.

Implementations of the invention may further include one or more of the following features. The exogenous agent contains preformed bubbles that have a mean diameter less than an upper size limit for being able to pass through a capillary bed of the subject. The exogenous agent has a concentration of bubbles high enough such that the blood-organ barrier will open in response to the applied energy.

In general, in another aspect, the invention provides a method of opening a blood-brain barrier of a subject. The method includes providing an exogenous agent configured to facilitate opening of the blood-organ barrier, administering the exogenous agent to a desired region of a brain of the subject, and applying ultrasound energy to the desired region of the brain of the subject while the exogenous agent is present in the desired region, the ultrasound energy being in a blood-brain-barrier-opening amount sufficient to induce opening of the blood-brain barrier of the subject with the exogenous agent present, the blood-brain-barrier-opening amount being below a damage amount sufficient to induce thermal damage to brain tissue of the subject, and the exogenous agent being administered to the subject in a non-invasive manner relative to a skull of the subject.

Implementations of the invention may include one or more of the following features. The blood-brain-barrieropening amount is less than approximately two orders of magnitude lower than the damage amount. The exogenous agent contains preformed gaseous bubbles. The energy applied is ultrasound energy and the exogenous agent contains at least one of a high concentration of gas, solid particles configured to vaporize in response to body temperature, solid particles configured to vaporize in response to the ultrasound energy, liquid configured to vaporize in response to body temperature, liquid configured to vaporize in response to the ultrasound energy, micro particles configured to act as cavitation sites, solid particles having higher acoustic impedance than tissue in the desired region, and liquid with a high ultrasound absorption coefficient.

In general, in another aspect, the invention provides a method of opening a blood-brain barrier of a subject, the method including providing an exogenous agent containing gaseous bubbles, administering the exogenous agent to a desired region of a brain of the subject, applying ultrasound energy to the desired region of the brain of the subject while the exogenous agent is present in the desired region, the ultrasound energy being in a blood-brain-barrier-opening amount sufficient to induce opening of the blood-brain barrier of the subject with the exogenous agent present, imaging at least the desired region of the brain of the subject, and determining if the blood-brain barrier has opened in the desired region using results of the imaging, the blood-brain-barrier-opening amount is below a damage amount sufficient to induce thermal damage to brain tissue of the subject, and the exogenous agent is administered to the subject in a non-invasive manner relative to a skull of the subject.

Implementations of the invention may include one or more of the following features. The applying includes adjusting at least one characteristic of the ultrasound energy to apply at least the blood-brain-barrier-opening amount to the desired region. The blood-brain-barrier-opening amount is less than approximately two orders of magnitude lower than the damage amount. The exogenous agent contains preformed bubbles that have a mean diameter less than an upper size limit for being able to pass through a capillary bed of the subject. The exogenous agent has a concentration of bubbles high enough such that the blood-brain barrier will open in response to the applied energy.

Various aspects of the invention may provide one or more of the following advantages. Ultrasound can be used to produce consistent focal blood-brain barrier opening leakage substantially without damage to surrounding brain tissue while using noninvasive image guidance and monitoring. Temporal average spatial peak powers of approximately two orders of magnitude below the level required for thermal damage of the brain tissue can be used while opening the blood-brain barrier (BBB). Local noninvasive targeted drug delivery, cell transplantation, gene therapy, or delivery of other substances with therapeutic or diagnostic use can be achieved in the brain or other organs in which drug delivery via the vasculature is limited. Undesired effects to non-targeted issues may be reduced and/or eliminated.

These and other advantages of the invention, along with the invention itself, will be more fully understood after a review of the following figures, detailed description, and claims.

DETAILED DESCRIPTION OF PREFERRED EMBODIMENTS

Figure 1:
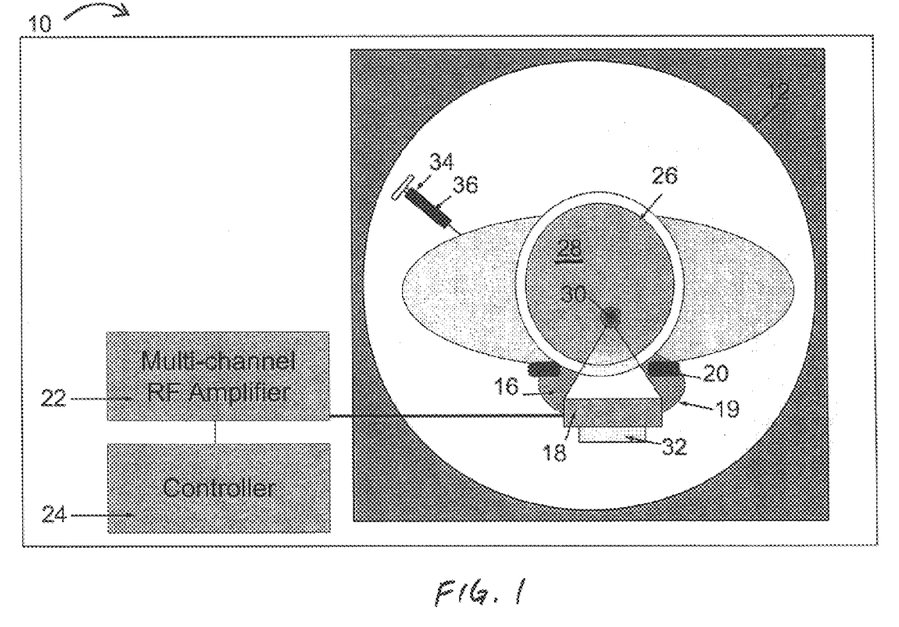
FIG. 1 is a schematic diagram showing a sonication arrangement.

Referring to FIG. 1, a noninvasive BBB-opening system 10 includes an imaging system 12 such as a Magnetic Resonance Imaging (MRI) or CT scanner, an enclosure 14 containing a coupling medium (such as water) 16 and an ultrasound transducer array 18, a Radio Frequency (RF) amplifier 22, and a controller 24 such as a personal computer. If the imaging system 12 is an MRI, then the BBB-opening system 10 will also include an MRI coil 20. The system 10 can be used to provide noninvasive therapy to a subject 26 (with only the subject's skull shown in FIG. 1). For example, the therapy could be to open the BBB in a brain 28 of the subject 26.

The imaging system 12 can provide MRI images of the subject's brain 28 noninvasively, specifically in an image plane 31. The imaging system 12 can be, e.g., a standard 1.5 Tesla Signa MRI system (made by General Electric Medical Systems, of Milwaukee, Wis.). The MRI coil 20 has a diameter such that the coil 20 can be placed around the subject's head to improve signal-to-noise ratio of the MRI scanner. Different coil designs or arrays of coils can also be used. The temperature-dependent proton resonant frequency shift can be estimated using a fast spoiled gradient echo sequence (FSPGR) or fast gradient echo (FGRASS). The imaging time is such that adequate temporal sampling of the temperature elevation during sonication of the subject 26 using the array 18 can be achieved.

Ultrasound energy is provided by an ultrasound subsystem including the array 18, the RF amplifier 22 (including a frequency generator, a phase and amplitude control unit, and a multi-channel RF-amplifier), and the controller 24. The ultrasound array 18 is configured to transmit ultrasound energy, and to have that energy focus in a desired region 30. Each element of the array 18 is driven with a similar but separate RF signal produced by the multi-channel amplifier 22 under control of the controller 24. The controller 24 regulates the amplitude, phase, and pattern of the signal (e.g., continuous, pulsed, etc.). For example, the RF signals from the elements of the array 18 can have relative phases and amplitudes such that skull-induced distortions are compensated for to induce a single focus at a desired location. The array 18 can be mounted on a positioning device 32 that can be adjusted to change the location of the focused ultrasound energy. Alternatively, the focus location can be adjusted electronically using different relative phase excitations of the array elements.

A syringe 34 contains an ultrasound contrast agent 36 to be injected into the subject 26. The agent 36 includes material that facilitates cavitation under low ultrasound energy levels that are insufficient to induce thermal damage to soft tissue, e.g., brain tissue (although not necessarily any soft tissue).

The agent 36 can contain preformed microbubbles of various sizes and in various concentrations. For example, bubbles preferably have a mean diameter lower than an upper limit that can pass through the capillary bed, this upper limit being approximately $1\times10^{-5}$ m. Some bubbles may exceed the upper size limit, but preferably enough bubbles are sized lower than the upper limit such that the agent 36 can effectively assist with opening the BBB. For example, the agent 36 can be Optison, made by Mallinckrodt Inc. of St. Louis, Mo., 63042, that contains micro bubbles. The micro bubbles of this agent have a mean diameter of $2.0\times10^{-6}$ m to $4.5\times10^{-6}$ m and a concentration of $5\times10^8$ bubbles/ml to $8\times10^8$ bubbles/ml. Concentrations of injected agent 36 of about $2.5\times10^8$ bubbles/ml to about $16\times10^8$ bubbles/ml have also proven effective. Concentrations preferably are high enough to assist with opening the BBB and low enough such that the agent 36 can be safely delivered via blood vessels, and low enough to avoid unacceptable amounts of bubbles combining are avoided or other effects that would inhibit performance of the agent 36.

The agent 36 can have characteristics other than preformed bubbles. The agent 36 can be a liquid containing preformed gas bubbles, or solid particles, or liquid droplets that contain a fluid, with a low enough vaporizing point that the solid particles or fluid will vaporize from body heat or due to the pressure or temperature effects caused by the ultrasound. The agent 36 may also be a liquid with high gas concentration or micro particles that can act as cavitation sites. The agent 36 may also be a liquid with solid particles that have a significantly different, higher, acoustic impedance than that of soft tissue. The agent 36 may also be a liquid with a high acoustic, e.g., ultrasound, absorption coefficient.

Figure 2:
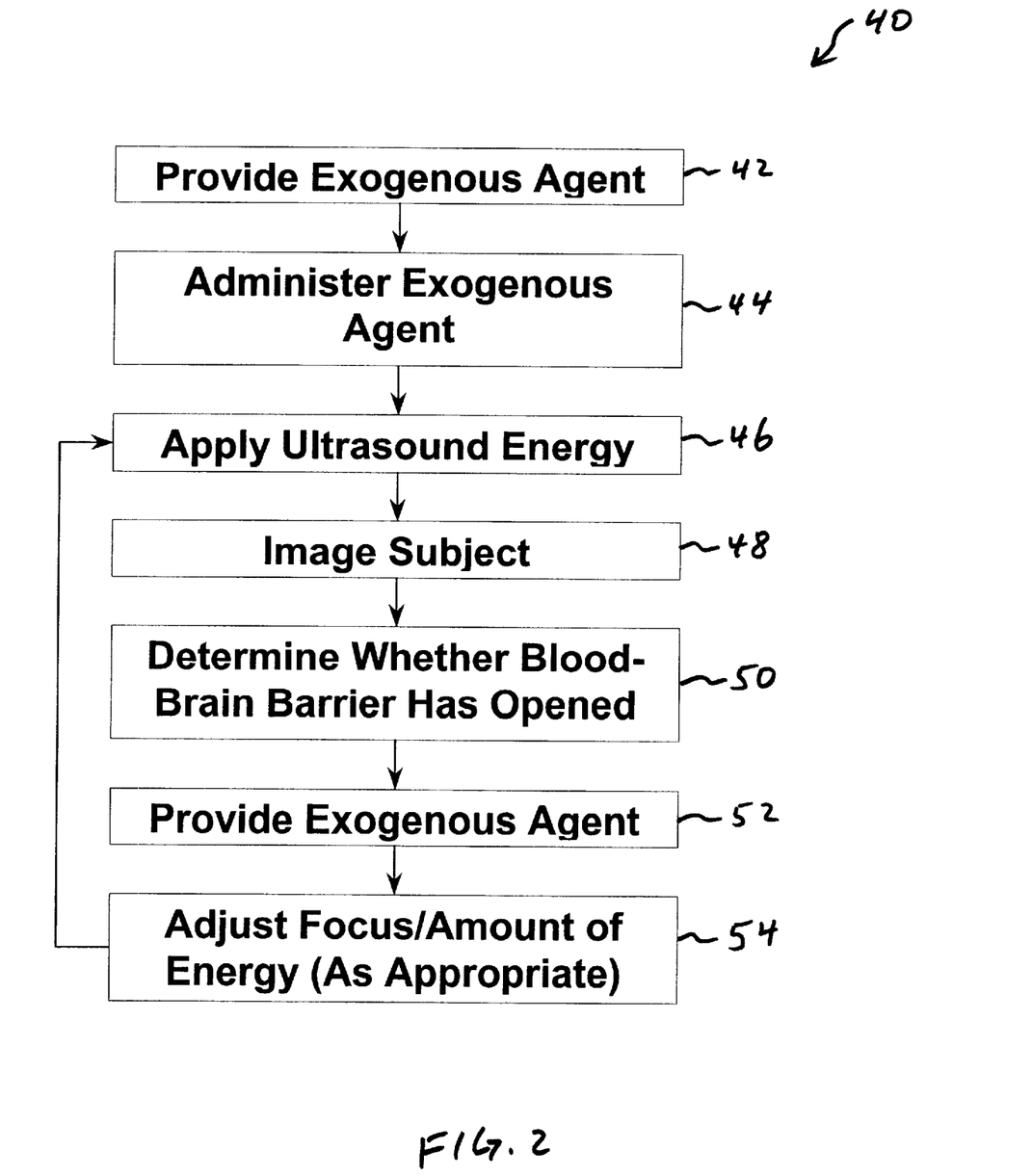
FIG. 2 is a block flow diagram of a process using the arrangement shown in FIG. 1.

Referring to FIG. 2, with further reference to FIG. 1, a process 40 of opening the BBB in the subject 26 uses the system 10 to apply focused ultrasound energy to the desired region 30 of the subject 26 containing the exogenous agent 36, for example, with the preformed micro-bubbles. It is believed that the acoustic energy provided by the ultrasound subsystem to the micro bubbles in the exogenous contrast agent injected into the subject's blood stream induces cavitation inside of blood vessels. It is further believed that this cavitation induces mechanical stresses that cause a transient increase in transmission of matter through the capillary wall in the brain 28, and thus a transient opening of the BBB.

At stages 42 and 44, the exogenous agent is provided and administered to the subject 26. The agent 36 contains micro bubbles, or material that can form bubbles in the blood stream under ultrasound exposure or body heat, or other material to interact with the ultrasound energy to help open the BBB. The agent 36 is administered at stage 44 by injection into the subject's vasculature using the syringe 34. For example, the syringe 34. can be inserted into a vein in the subject's arm, thus being noninvasive relative to the subject's skull. The agent 36 could also be injected via a catheter into a subject's artery. A sufficient time is allowed to pass for the agent 36 to travel through the subject's vasculature to reach the desired region 30 in the subject's brain 28.

At stage 46, ultrasound energy is applied by the ultrasound subsystem, to the subject 26, and preferably to the desired region 30 of the subject's brain 28. This energy is applied without opening the subject's skull. The controller 24 indicates to the amplifier 22 energy to provide to the array 18, including how much, and in what pattern (e.g., frequency, phase, amplitude, number of cycles, duty cycle) to provide energy using the array 18 to the subject 26. In response to the indications from the controller 24, the amplifier 22 conveys energy to the array 18. Preferably, the acoustic energy from the array 18 is of an amount, e.g., an average amount, that will induce opening of the BBB, but not cause thermal or other damage to the subject's brain tissue (although the energy amount provided could be sufficient induce thermal damage if it is desirable to do so). For example, the temporal average spatial peak power can be approximately two orders of magnitude below a level that will induce thermal damage to the subject's brain tissue, or lower.

The array 18 transmits the energy as acoustic energy through the subject's skull and into the subject's brain 28. Relative excitations of the portions of the array 18, as well as physical characteristics of the subject's skull and brain 28, determine where the ultrasound energy from the array 18 will focus.

At stages 48 and 50, the subject 26 is imaged and it is determined whether the ultrasound subsystem properly focused sufficient ultrasound energy to open the BBB of the subject 26 in the desired region 30. Whether the BBB opened is determined by evaluating the signal intensity change in the MRI signal during the sonication or contrast enhancement in the desired region 30 caused by an MRI or CT contrast agent that is injected in the blood stream, with significant enhancement indicating BBB opening. It may also be possible to perform opening of the BBB without image monitoring based on predetermined sonication parameters.

At stages 52 and 54, additional agent 36 is provided as appropriate and the energy applied by the ultrasound subsystem is adjusted as appropriate to open the BBB in the desired region 30. Various parameters of the energy applied can be adjusted. For example, the focus of the energy can be changed, e.g., by altering the relative phase excitations of the portion of the array 18. Also, amounts of energy can be adjusted, e.g., frequency, burst length, peak pressure, average power, duty cycle of a pulse train, number of bursts, and/or repetition frequency of bursts. Stages 46, 48, and 50 can be repeated, or performed concurrently with stages 52 and 54, so that these adjustments are made in conjunction with stages 46, 48, and 50 to obtain BBB opening in the desired region 30.

Experimental Implementation

Ultrasound Equipment

Ultrasound fields were generated by a spherical sixteen sector focused, piezoelectric transducer with a 100-mm diameter, an 80-mm radius of curvature, and a resonant frequency of 1.63 MHz as the array 18. Each sector was driven with an identical but separate RF signal generated by the multi-channel driving system 22 under control of a computer. For these experiments, the RF signals were in phase and equal in amplitude.

The properties of the transducer were measured in a separate apparatus. The acoustic power output as a function of applied RF power was measured using a radiation force technique. The ultrasound field distributions were measured using a needle hydrophone (0.075 mm in diameter, made by Precision Acoustics, of Dorchester, UK). The absolute intensity in water was measured using a PVDF (polyvinylidene fluoride) coplanar shielded membrane hydrophone (made by GEC-Marconi Research Center, of Chelmsford, England) with an active area of 0.5 mm in diameter. This hydrophone was calibrated by the National Physics Laboratory, Teddington, Middlesex, England. These measurements were performed in water at the two lowest pressure amplitude values available from the amplifier system and then extrapolated based on the measured acoustic power. Estimates for the pressure amplitude in the brain 28 were obtained by decreasing the measured water values by a factor of 0.85, based on ultrasound attenuation through 10 mm of brain with an average attenuation coefficient of 5 Np/m/MHz.

Sonications were performed under MRI guidance and monitoring. The transducer array 18 was mounted on an experimental positioning device (made by TxSonics, Inc, of Haifa, Israel) integrated in the MRI scanner table. For these experiments, the positioning system was used only to move the transducer. Sonication-related aspects were executed by an external PC that controlled the sonications via the multi-channel amplifier system 22.

Animals

New Zealand white rabbits had there BBBs opened using the setup described above. Eleven New Zealand white rabbits (approximately 4 kg, males) were anesthetized by a mix of 40 mg/kg ketamine (made by Aveco Co, Inc, of Fort Dodge, Iowa), and 10 mg/kg of xylazine (made by Lloyd Laboratories, of Shenandoah, Iowa). A piece of skull (approximately 15×15 mm) was removed, and the skin was replaced over the craniotomy. The brain sonications were executed after the wound healed and all of the air was dissolved (a minimum of 10 days after the surgery). The bone was removed to simplify the experiments. If the bone was in place, the array 18 would be excited to compensate for the bone. The animals were placed on their backs on a water blanket that circulated temperature controlled water to maintain the body temperature of the animal. The head was fixed in the treatment position by an acrylic holder. The skin (hair removed) on the top of the head was coupled to the water bath that contained the transducers with a degassed water bag 19 (FIG. 1).

Sonications

T2-weighted images were obtained to localize the craniotomy and to confirm a clear beam path to the desired target depth. Before the experimental sonications, a low power (acoustic power=1.1 W) continuous wave sonication for 10 s was executed while obtaining MRI thermometry. This is about 40% of the power shown necessary to produce brain damage in the same experimental conditions. The focal spot was visible in all cases and could be compared to the target location. Often a small (typically less than 1 mm) correction was performed to align the target location with the focus of the ultrasound energy. After alignment, four or six locations were sonicated with the focus aimed at 10 mm deep in the brain 28 at different peak power levels that ranged from 0.2 to 11.5 W (acoustic power). These levels translate to an acoustic temporal and spatial peak intensity range of 14 to 590 W/cm$^2$. The sonications were pulsed with burst lengths of 10 or 100 ms with a repetition frequency of 1 Hz. Thus, the temporal average power (directly proportional to the temperature elevation in the tissue) during the sonication was $\frac{1}{10}$ or $\frac{1}{100}$ of the peak acoustic power. The duration of the whole sonication was 20 s. These parameters were based on preliminary in vivo experiments that searched for controlled, focal opening of the BBB.

Approximately 10 s prior to the start of the sonication, a bolus of ultrasound contrast agent (Optison, made by Mallinckrodt Inc. of St. Louis, Mo., 63042) that contained micro bubbles (mean diameter=$2.0-4.5\times10^{-6}$ m; concentration=$5-8\times10^8$ bubbles/ml) was injected in the ear vein of each rabbit. The injected volume was selected to be 0.05 ml/kg, which is in the range (0.5 ml–5 ml) recommended for human use by the manufacturer. The bolus was flushed from tubing of an injection device by injecting approximately 1 ml of saline. The sonications in different locations with new injections were performed with 5–10 min. delays that allowed the bubbles to clear from the circulation of the rabbit.

The animals were sacrificed between 4 hours and 7 days after the sonication and the brains were fixed in formalin. Whole-brain evaluation was conducted by sectioning the brain 28 and performing a microscopic investigation. The brain 28 was sectioned at 6 micrometers (across the beam direction; parallel to the MRI slices), and every 20$^{th}$ section (interval of 0.4 mm) was stained by hematoxylin and eosin.

MRI

The MRI scanner was a standard 1.5 Tesla Signa system (made by General Electric Medical Systems, of Milwaukee, Wis.). A 7.5 cm diameter surface coil was placed under the head to improve the signal-to-noise ratio. The temperature dependent proton resonant frequency shift (18) was estimated using a fast spoiled gradient echo sequence (FSPGR) or fast gradient echo (FGRASS) with the following imaging parameters: repetition time (TR)=40.9 ms, echo time (TE)=19.9 ms, flip angle=30°, bandwidth (BW)=3.57 kHz, resolution 256×128, field of view (FOV)=12 cm×9 cm, slice thickness=3 mm. The bandwidth helped with controlling the TE in the product sequence and thus, the imaging time in the FSPGR sequence. The TE was selected so that adequate temporal sampling of the temperature elevation during the sonication could be achieved. Twenty images were obtained in a series with the total acquisition time of 80 s. The first image was triggered 4 s prior to the start of the contrast injection sonication. The scanner was programmed to reconstruct the magnitude, real and imaginary images for each of these time points. The real and imaginary parts were used to calculate the phase difference between the two time points. The scan plane was located across the focus at the focal depth.

After the sonications, T1-weighted images were obtained by using a Fast Spin Echo (FSE) pulse sequence. For these images, the following parameters were used: TR=500 ms, TE=17 ms, echo train length=4, three data acquisition, field of view=10 cm and matrix size of 256×256, slice thickness of 1.5 mm interleaved, BW=16 kHz. These scans were repeated after a bolus of gadopentetate dimeglumine contrast agent (MAGNEVIST, made by Berlex Laboratories Inc, of Wayne, N.J.) (molecular weight of 928) was injected into the ear veins of the rabbits (dose 0.125 mmol/kg) to evaluate the BBB opening. A T2-weighted FSE sequence was used to determine edema in the brain tissue with the following parameters: TR=2000 ms, TE=17 and 115 ms, echo train length=8, 2 data acquisitions, field of view=10 cm, slice thickness=1.5 mm. The follow up MRI studies were repeated two days after the sonications in most cases. In one case, imaging was also performed at one day, and in two cases the imaging was performed at seven days.

Signal Analysis

The level of contrast enhancement was measured in the focal spot by averaging the signal intensity over a 3×3 set of voxels (1.17×1.17 mm) and normalizing the value to the baseline value before contrast injection. The signal also was averaged outside of the sonicated location to obtain control values.

Results

Figure 3:
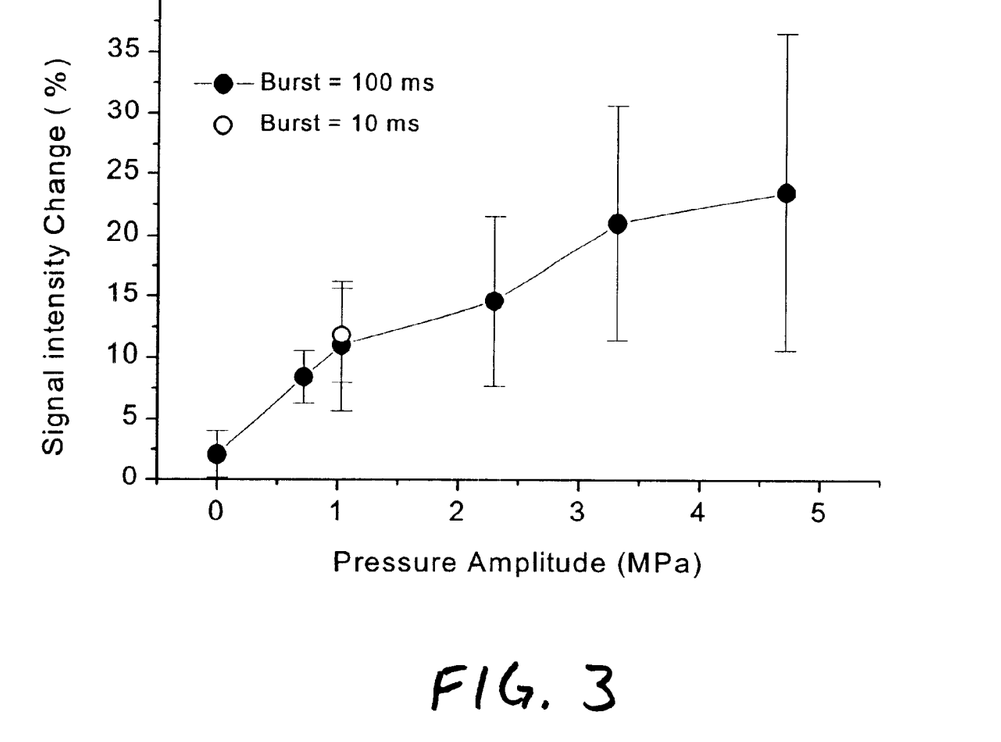
FIG. 3 is a graph of normalized signal intensity (SI) change at focal volumes in a rabbit brain after a last sonication, using the arrangement shown in FIG. 1, as a function of pressure amplitude during 100 ms ultrasound bursts.
Figure 4:
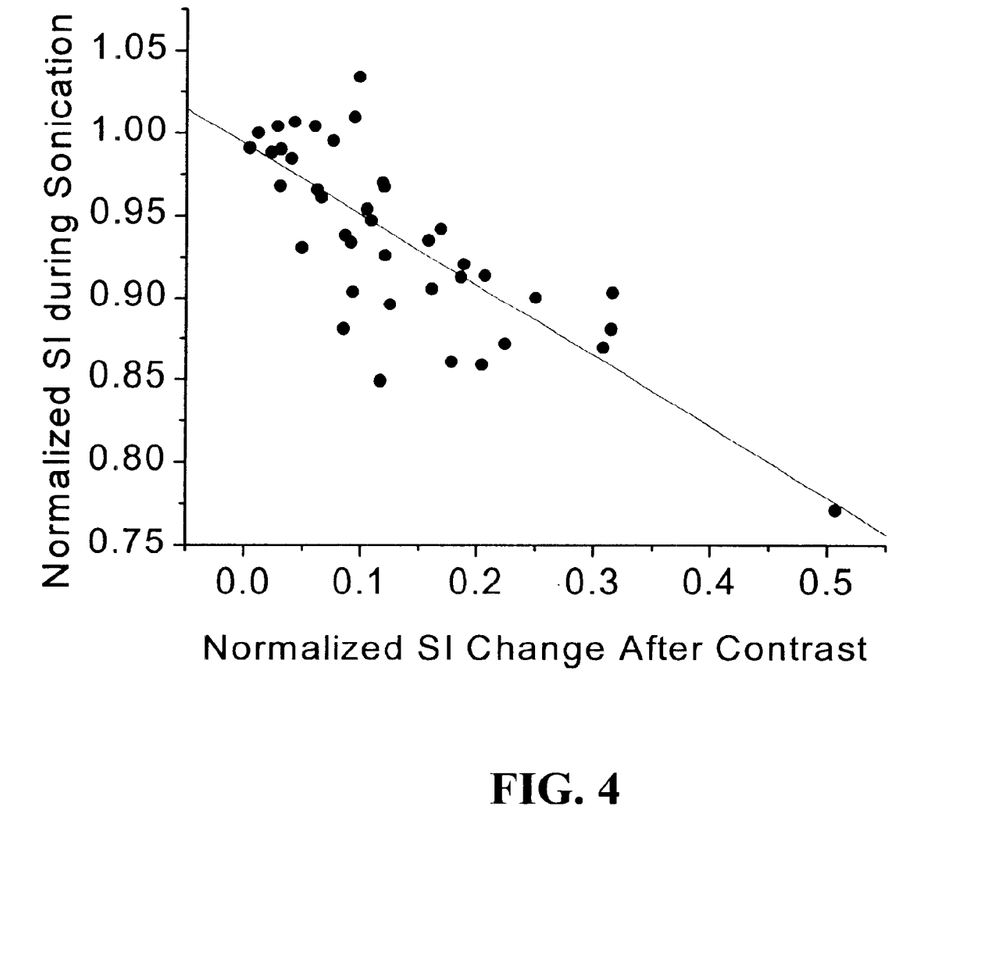
FIG. 4 is a graph of normalized signal intensity increase caused by contrast injections at a sonicated location vs. normalized signal intensity of an SPGR sequence during sonication.

Pulsed sonication produced focal BBB opening without damage to the tissue in the beam path as determined by contrast enhanced MRI scans. The signal intensity (SI) change in the T1-weighted images caused by leakage of the contrast agent into the brain was dependent on the applied acoustic pressure amplitude as shown in FIG. 3. The BBB opening, however, did not appear to be burst-length or average-acoustic-power dependent as the sonications with 10 ms and 1 ms bursts (i.e. 10% and 1% duty cycle) produced approximately equal enhancement. The SPGR magnitude images acquired during the sonications showed a reduction in the SI at the focal location. This reduction remained after the sonication and was pressure-amplitude dependent and correlated with the contrast enhancement observed after the sonications as shown in FIG. 4. The normalized signal intensity increased at the sonicated locations after an MRI contrast injection vs. the normalized signal intensity in the FSPGR acquired during the sonications. The signal intensity decrease in the FSPGR images acquired during the sonications decreased proportionally to the signal intensity increase after the MRI contrast injections. Thus, it correlated with the BBB opening. Thus, online imaging may be used to determine when the BBB is open or perhaps even to quantify the opening during the sonications. The average maximum temperature elevations measured during the sonications by the temperature sensitive phase imaging were 4.8+/−1.7° C., 3.4+/−0.9° C., and 2.3+/−0.8° C. for 11.5, 5.8, and 2.7 W peak acoustic power respectively. These temperature elevations are below the threshold for thermal tissue damage.

The BBB was consistently opened with the sonications except about half of the sonications with the lowest power level. The contrast-enhanced imaging was repeated up to six hours after the sonication during the day of the sonication (six locations) and the BBB was still open at that point. No contrast enhancement, however, was evident in the rabbit imaged 1 day after the sonications. Similarly, the contrast enhancement was not present at 2 or 7 days except in a few of the high power sonications that produced neuron damage.

Figure 5:
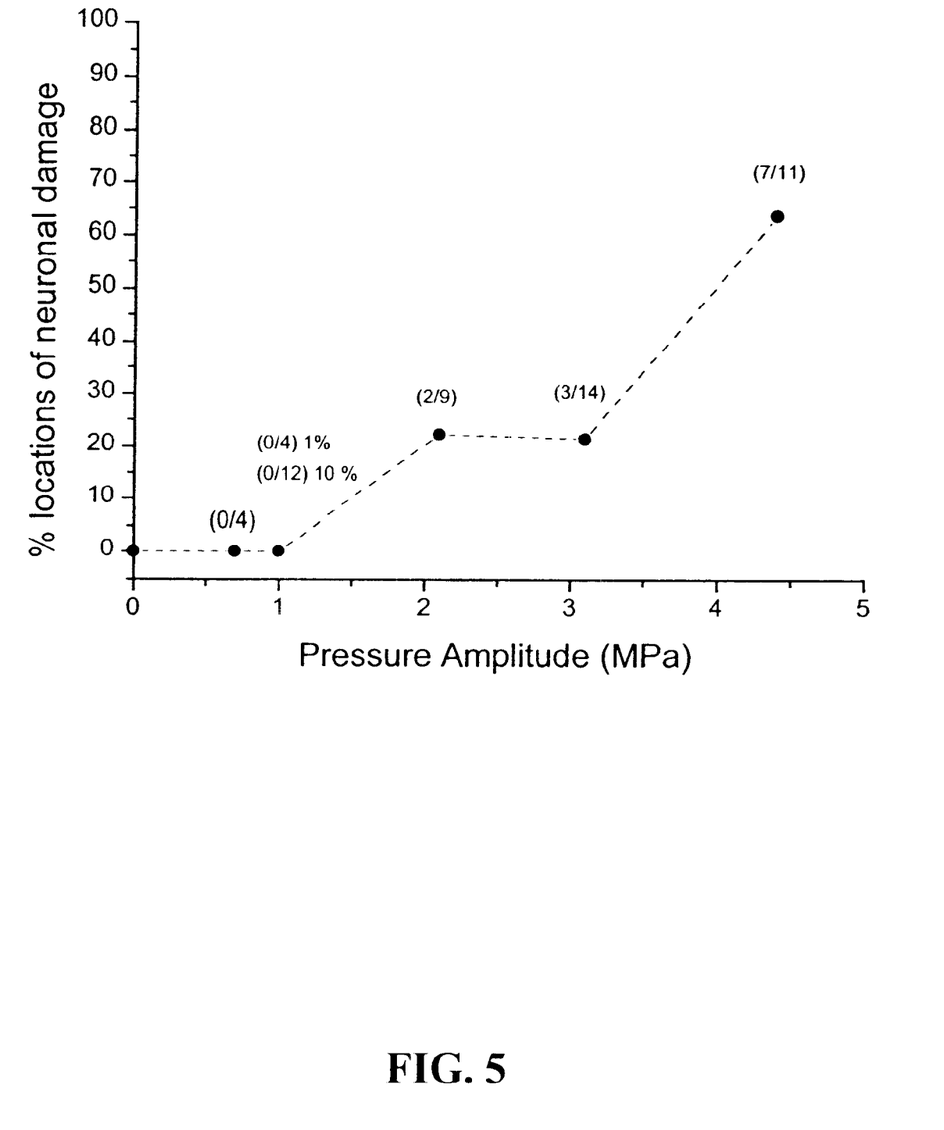
FIG. 5 is a graph of percentage of focal locations that showed neuronal damage as a function of pressure amplitude of sonication.

The histology evaluation showed damage to the neurons in approximately 60% of the sonicated locations at the highest power level used as shown in FIG. 5. At pressure amplitudes between 2–3 MPa, the percentage of the neuron damage was approximately 20%. There was no neuron damage at the lowest three exposure levels. In many cases, however, the sonicated locations showed red blood cells in the brain tissue outside of the blood vessels, indicating vascular damage. The brains examined after 7 days survival did not show any tissue damage.

Discussion

The experiments demonstrate that focused ultrasound can be used to produce consistent focal BBB leakage without, or substantially without, damage to the surrounding brain tissue while using noninvasive image guidance and monitoring. The above-described experiments were able to produce the BBB opening consistently by using an ultrasound contrast agent with gas bubbles as cavitation sites. The temporal average spatial peak powers used were approximately two orders of magnitude below the level that induces thermal damage of the brain tissue. These power levels can be reached through the skull by using phased array applicators that compensate for skull induced distortions.

The BBB opening allowed an MRI contrast agent with molecular weight 928 to enter into the brain. Thus, many of the chemotherapeutic agents usable for brain tumor treatments (molecular weight between 200 and 1200) could enter into the brain through the ultrasound-induced deficit.

In the exemplary experiments, the maximum temperature elevation from the pulsed sonication at the highest power level used was approximately 5° C. with the ultrasound contrast agent and undetectable without it. This indicates that cavitation events increase the local temperature elevation. In the exemplary experiments, the lowest temporal average acoustic power level that consistently produced BBB opening was approximately 200 times lower than the highest power used. MRI temperature measurements did not show any temperature rise for these sonications, indicating that it would be less than the 1–2° C. noise level of the MRI thermometry used in the experiments. If the temperature elevation is linearly proportional to the applied acoustic power, then the temperature elevation was approximately 0.025° C. during these low power sonications.

The correlation between reduction in the signal intensity of an SPGR sequence and the opening of the BBB can be used to perform on-line monitoring of the exposures. Since the SI change remained visible over the course of the sonications (up to 60 min.) it was not caused by temperature elevation, but could be due to a susceptibility change induced by extravascularized red blood cells.

The lowest pressure amplitude level used was less than 0.7 MPa, indicating that similar events may be detected by using diagnostic ultrasound exposures. This may be a safety concern when brain imaging is performed using ultrasound contrast agents containing microbubbles.

Other embodiments are within the scope and spirit of the appended claims. For example, different apparatus, e.g., the ultrasound array 18, than used for the experiments described above can be used in the setup of FIG. 1. Also, the process shown in FIG. 2 can be altered, e.g., by having stages added, removed, or rearranged. The experiments conducted are exemplary and not limiting. Thus, maxima and/or minima described are not necessarily the achievable maxima and/or minima using the invention. Although the BBB is referred to predominantly above, the invention may be applied to other blood-organ barriers.

Figure 6:
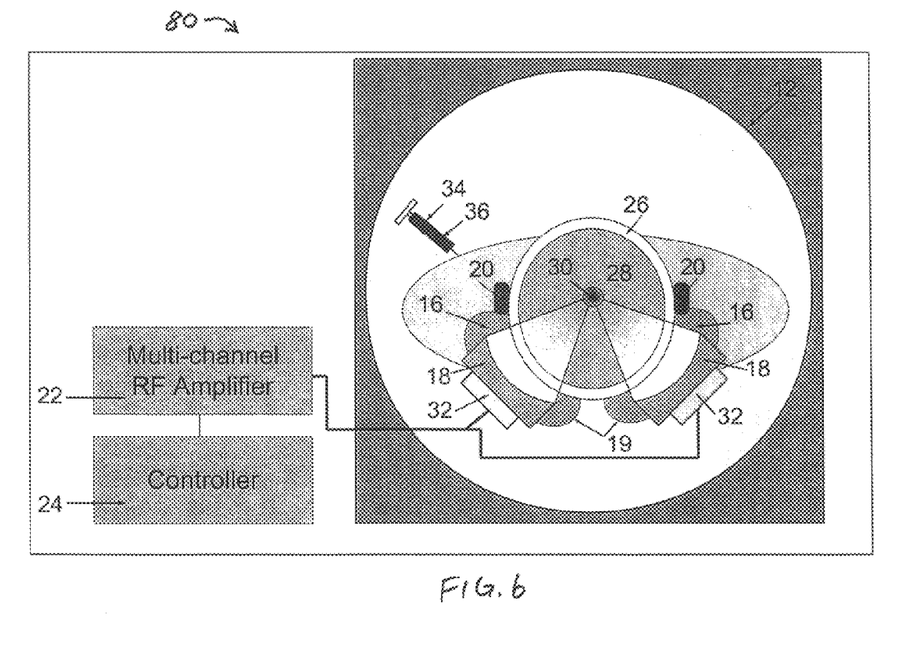
FIGS. 6–7 are schematic diagrams showing alternative sonication arrangements.
Figure 7:
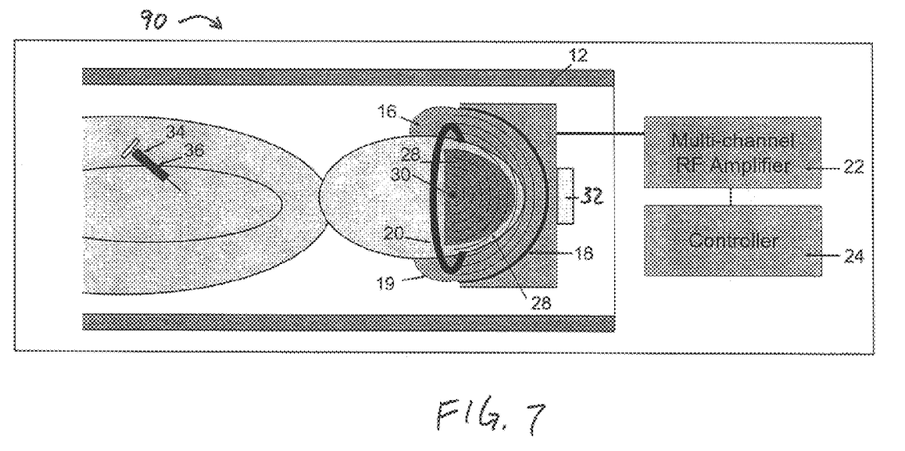

Other arrangements for the array 18 than that shown in FIG. 1 are acceptable. Referring to FIG. 6, another noninvasive BBB-opening system 80 includes similar features as that of FIG. 1, with the array 18 split into multiple portions. As shown, the array 18 has two portions physically separated and directing energy to the common desired region 30. Other features, such as the positioning device 32 and coupling medium 19 are modified accordingly. Referring to FIG. 7, in another noninvasive BBB-opening system 90, the array 18 is approximately hemispherical and partially encloses/surrounds the subject's head. The ultrasound can also de delivered via interstitial or intravascular catheters, or applicators used during surgery. Non-focused ultrasound fields may also be used if BBB opening of a large region is desired. These fields can be produced with transducer arrays or with single element applicators. Focusing can also be achieved by pulsing the ultrasound sources with predetermined delays such that the pressure pulses will interfere and produce a focus in the desired location. The ultrasound can also be delivered from an ultrasound system designed for diagnostic or other purposes. The ultrasound waves used can be of one or multiple frequencies.

What is claimed is:

1. A method of opening a blood-brain barrier of a subject, the method comprising:

providing an exogenous agent configured to facilitate opening of the blood-brain barrier;

administering the exogenous agent to a desired region of the brain; and applying energy to the desired region of the subject while the exogenous agent is present in the desired region, the energy being in a blood-brain-barrier-opening amount that will induce opening of the blood-brain barrier of the subject with the exogenous agent present and the blood-brain-barrier-opening amount being below a damage amount that will induce thermal damage to tissue.

2. The method of claim 1 wherein the energy applied is ultrasound energy; and wherein the exogenous agent contains at least one of gaseous bubbles, a high concentration of gas, solid particles configured to vaporize in response to body temperature, solid particles configured to vaporize in response to the ultrasound energy, liquid configured to vaporize in response to body temperature, liquid configured to vaporize in response to the ultrasound energy, micro particles configured to act as cavitation sites, solid particles having higher acoustic impedance than tissue in the desired region, and liquid with a high acoustic absorption coefficient.

3. The method of claim 1 wherein the blood-brain-barrier-opening amount is less than approximately ten times lower than an amount that will induce damage to tissue in the absence of the exogenous agent.

4. The method of claim 3 wherein the blood-brain-barrier-opening amount is less than approximately one hundred times lower than an amount that will induce damage to tissue in the absence of the exogenous agent.

5. The method of claim 3 wherein the blood-brain-barrier-opening amount is a temporal average power.

6. The method of claim 5 wherein the blood-brain-barrier-opening amount is less than approximately 200 times lower than an amount that will induce damage to tissue in the absence of the exogenous agent.

7. The method of claim 1 wherein the exogenous agent is administered to the subject without penetrating a skull of the subject.

8. The method of claim 7 wherein the exogenous agent is administered through a vasculature of the subject.

9. The method of claim 8 wherein the administering includes waiting for the exogenous agent to reach the desired region via the vasculature.

10. The method of claim 1 further comprising imaging at least the desired region of the subject and determining if the blood-brain barrier has opened in the desired region using results of the imaging.

11. The method of claim 10 wherein the applying includes adjusting at least one characteristic of the ultrasound energy to apply at least the blood-brain-barrier-opening amount to the desired region.

12. The method of claim 1 wherein the exogenous agent contains preformed bubbles that have a mean diameter less than an upper size limit for being able to pass through a capillary bed of the subject.

13. The method of claim 1 wherein the exogenous agent has a concentration of bubbles high enough such that the blood-brain barrier will open in response to the applied energy.

14. A method of opening a blood-brain barrier of a subject, the method comprising:

providing an exogenous agent configured to facilitate opening of the blood-brain barrier;

administering the exogenous agent to a desired region of a brain of the subject; and applying ultrasound energy to the desired region of the brain of the subject while the exogenous agent is present in the desired region, the ultrasound energy being in a blood-brain-barrier-opening amount that will induce opening of the blood-brain barrier of the subject with the exogenous agent present;

wherein the blood-brain-barrier-opening amount is below a damage amount that will induce thermal damage to brain tissue of the subject; and wherein the exogenous agent is administered to the subject in a non-invasive manner relative to a skull of the subject.

15. The method of claim 14 wherein the blood-brain-barrier-opening amount is less than approximately one hundred times lower than an amount that will induce damage to tissue in the absence of the exogenous agent.

16. The method of claim 15 wherein the blood-brain-barrier-opening amount is a temporal average power.

17. The method of claim 16 wherein the blood-brain-barrier-opening amount is less than approximately 200 times lower than an amount that will induce damage to tissue in the absence of the exogenous agent.

18. The method of claim 14 wherein the exogenous agent contains performed gaseous bubbles.

19. The method of claim 14 wherein the energy applied is ultrasound energy; and wherein the exogenous agent contains at least one of a high concentration of gas, solid particles configured to vaporize in response to body temperature, solid particles configured to vaporize in response to the ultrasound energy, liquid configured to vaporize in response to body temperature, liquid configured to vaporize in response to the. ultrasound energy, micro particles configured to act as cavitation sites, solid particles having higher acoustic impedance than tissue in the desired region, and liquid with a high ultrasound absorption coefficient.

20. A method of opening a blood-brain barrier of a subject, the method comprising:

providing an exogenous agent containing gaseous bubbles;

administering the exogenous agent to a desired region of a brain of the subject;

applying ultrasound energy to the desired region of the brain of the subject while the exogenous agent is present in the desired region, the ultrasound energy being in a blood-brain-barrier-opening amount that will induce opening of the blood-brain barrier of the subject with the exogenous agent present;

imaging at least the desired region of the brain of the subject; and determining if the blood-brain barrier has opened in the desired region using results of the imaging;

wherein the blood-brain-barrier-opening amount is below a damage amount that will induce thermal damage to brain tissue of the subject; and wherein the exogenous agent is administered to the subject in a non-invasive manner relative to a skull of the subject.

21. The method of claim 20 wherein the applying includes adjusting at least one characteristic of the ultrasound energy to apply at least the blood-brain-barrier-opening amount to the desired region.

22. The method of claim 21 wherein the blood-brain-barrier-opening amount is less than approximately two orders of magnitude lower than the damage amount.

23. The method of claim 22 wherein the exogenous agent contains preformed bubbles that have a mean diameter less than an upper size limit for being able to pass through a capillary bed of the subject.

24. The method of claim 23 wherein the exogenous agent has a concentration of bubbles high enough such that the blood-brain barrier will open in response to the applied energy.

25. The method of claim 22 wherein the blood-brain-barrier-opening amount is a temporal average power.

26. The method of claim 25 wherein the blood-brain-barrier-opening amount is less than approximately 200 times lower than an amount that will induce damage to tissue in the absence of the exogenous agent.

* * * * *

UNITED STATES PATENT AND TRADEMARK OFFICE
CERTIFICATE OF CORRECTION

PATENT NO.    : 6,514,221 B2                                              Page 1 of 1
DATED         : February 4, 2003
INVENTOR(S)   : Kullervo H. Hynynen et al.

It is certified that error appears in the above-identified patent and that said Letters Patent is hereby corrected as shown below:

Column 12,
Lines 61-63, claim 22 should read:
22. The method of claim 21 wherein the blood-brain-barrier opening amount is less that approximately one hundred times lower than an amount that will induce damage to tissue in the absence of the exogenous agent.

Signed and Sealed this

Twelfth Day of August, 2003

JAMES E. ROGAN
*Director of the United States Patent and Trademark Office*